US009527082B2

(12) United States Patent
Anson-Smith

(10) Patent No.: US 9,527,082 B2
(45) Date of Patent: Dec. 27, 2016

(54) PERMANENTLY SEALABLE NON-REUSABLE TIME CAPSULE, CONTAINER OR VESSEL

(76) Inventor: Brian Anson-Smith, Glastonbury (AU)

( * ) Notice: Subject to any disclaimer, the term of this patent is extended or adjusted under 35 U.S.C. 154(b) by 308 days.

(21) Appl. No.: 14/346,975

(22) PCT Filed: Mar. 23, 2012

(86) PCT No.: PCT/AU2012/000308
§ 371 (c)(1),
(2), (4) Date: Mar. 25, 2014

(87) PCT Pub. No.: WO2013/049874
PCT Pub. Date: Apr. 11, 2013

(65) Prior Publication Data
US 2014/0219890 A1    Aug. 7, 2014

(30) Foreign Application Priority Data

Oct. 3, 2011    (AU) .................................. 2011904069

(51) Int. Cl.
*B01L 3/14*    (2006.01)
*B01L 3/00*    (2006.01)
*A01N 1/02*    (2006.01)

(52) U.S. Cl.
CPC ............. *B01L 3/523* (2013.01); *A01N 1/0236* (2013.01)

(58) Field of Classification Search
CPC .. A61B 10/0096; B01L 3/508; B01L 3/50825; B01L 2300/042
USPC ........................................ 422/547, 550, 568
See application file for complete search history.

(56) References Cited

U.S. PATENT DOCUMENTS

| 4,665,668 A | 5/1987 | Serpico |
| 5,289,915 A | 3/1994 | Queen |
| 5,312,008 A | 5/1994 | Davis |
| 5,603,401 A * | 2/1997 | Brunner ................. B65D 25/16 206/204 |

(Continued)

FOREIGN PATENT DOCUMENTS

| CN | 2310568 | 3/1999 |
| CN | 201030016 | 3/2008 |

(Continued)

OTHER PUBLICATIONS

International Search Report and Written Opinion of the International Authority.

*Primary Examiner* — Jill Warden
*Assistant Examiner* — Dwayne K Handy

(57) ABSTRACT

The present invention relates to time capsules, vessels or containers, in particular but not limited to a permanently sealable non-reusable time capsule, vessel or container for storing a biological sample containing DNA for a prolonged period of time. The time capsule comprising a thick-walled vessel or container having a void or chamber with a tapered entry adapted to house glass vials containing the item of interest, a plug having a complementary external tapered configuration corresponding to the tapered entry, the tapered plug and entry having opposed peripheral grooves that are aligned when the plug is positioned in the vessel and a hard setting compound used to seal the plug forms a keyed ring in the opposing grooves to permanently and hermetically seal the plug in the vessel.

8 Claims, 1 Drawing Sheet

(56) References Cited

U.S. PATENT DOCUMENTS

| | | | |
|---|---|---|---|
| 5,957,125 A * | 9/1999 | Sagstetter | A61M 15/009 128/200.23 |
| 5,987,720 A | 11/1999 | Yamamoto | |
| 6,414,663 B1 | 7/2002 | Manross | |
| 7,367,450 B2 | 5/2008 | Maglione | |
| 7,861,385 B1 | 1/2011 | Meyer | |
| 2005/0005409 A1 | 1/2005 | Elnatan | |
| 2005/0081561 A1 | 4/2005 | Eggleston | |
| 2011/0208609 A1 | 8/2011 | Destephen | |

FOREIGN PATENT DOCUMENTS

| | | |
|---|---|---|
| EP | 1557475 | 7/2005 |
| GB | 2325922 | 12/1998 |
| JP | 2003292053 | 10/2003 |
| KR | 20030001050 | 1/2003 |
| WO | WO2007098570 | 9/2007 |

* cited by examiner

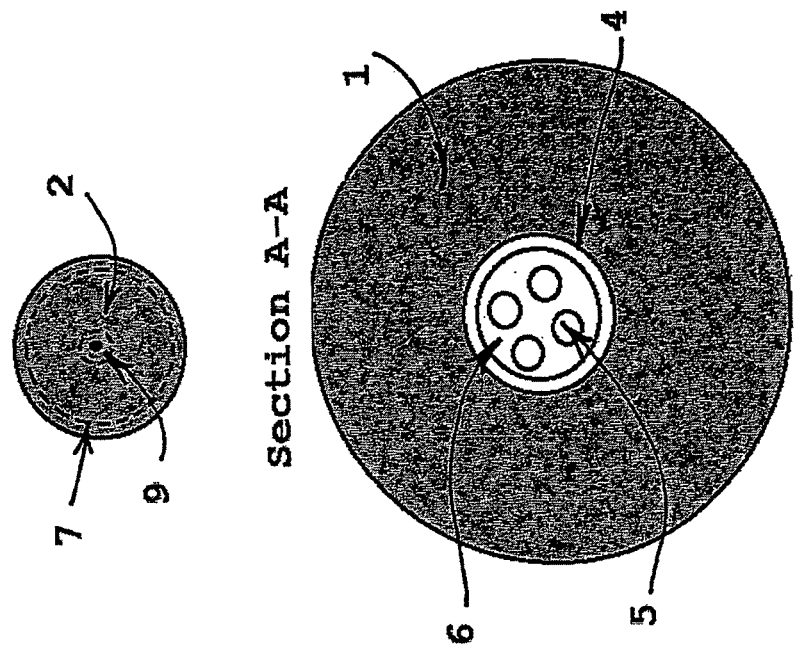
Figure 2
Plan veiw
Figure 3
Section A-A
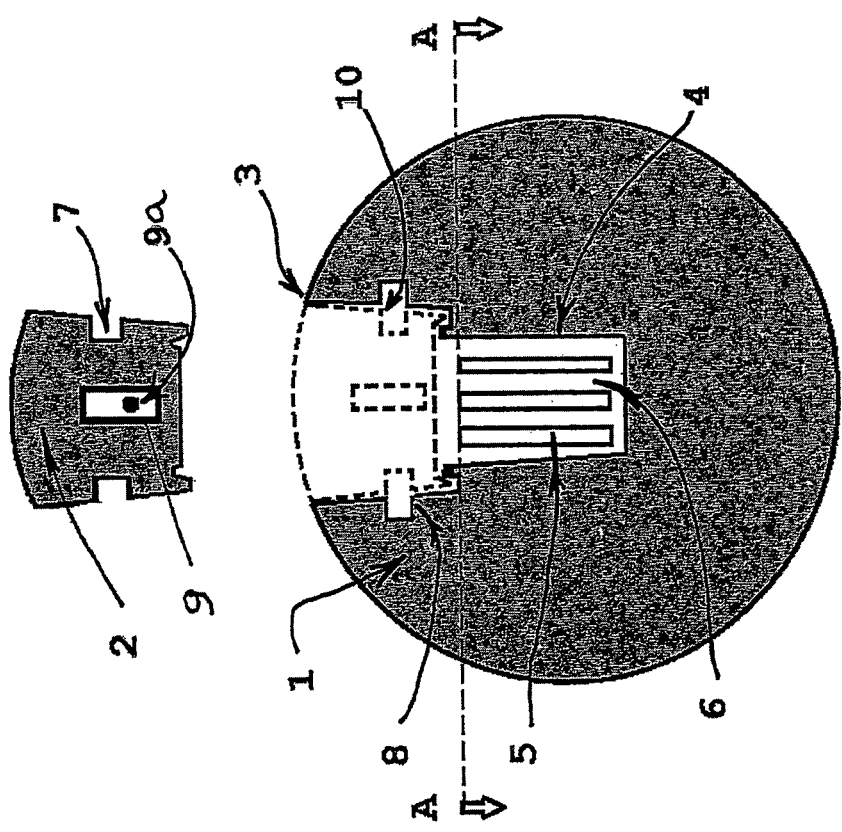
Figure 1

PERMANENTLY SEALABLE NON-REUSABLE TIME CAPSULE, CONTAINER OR VESSEL

FIELD OF THE INVENTION

The present invention relates to time capsules, vessels or containers, in particular but not limited to a permanently sealable non-reusable time capsule, vessel or container for storing at least one biological sample containing DNA for a prolonged period of time.

BACKGROUND OF THE INVENTION

Traditional containers, capsules or vessels of various styles and made from many different materials have for many years been utilized under the term 'time capsules' and have in a general sense been used extensively in the prior art. The general premise of a 'time capsule' is that items of significance or value are placed in an internal void of the container, subsequently temporarily sealed and then buried or stored for a predetermined period of time. Once the predetermined period of time has lapsed the time capsule is intended to be then opened so as to reveal the contents from within the internal void. Commonly, a time capsule contains items of particular relevance at the time of being buried such that the person opening the capsule in the future will gain knowledge and understanding of past community history. However, it is understood that in a broad sense a 'time capsule' can be regarded as a container for storing at least one object chosen to be of relevance to only the depositor and then stored or buried for an indefinite period of time with no intended future discovery date.

There is no doubt that the art of sealing objects of historical or cultural interest in traditional conveniently available containers has been well known and practiced throughout history. For example, the ancient Egyptians culturally believed that preserving and mummifying parts of the body and subsequently storing the same in urns was a manner in which immortality and/or heavenly ascension could be achieved. The problem was however, although the urns were protected by strong underground tombs the Egyptians failed in this endeavour partly because the containers had high value to tomb robbers, who after disposing of the original contents, sold (recycled) the urns on to other users for the same purpose.

In present day culture it is commonly known to use carefully crafted and intricate containers or urns for depositing the remains of deceased loved ones as a memorial for grieving relatives. (i.e. ashes from a cremation) A problem associated with this type of memorial storage technique is that crematoriums have been known to often confuse the ashes of different persons whereby relatives are not in fact provided with the remains of their particular loved-ones. While these types of containers are intended to contain an item of significant sentimental value they are all by their traditional use configuration designed to be reopened, therefore in no instance are those containers capable of being sealed permanently for extremely long periods of time and thus are short term time-capsule examples of containers used to temporarily house the contents until recycling, therefore not considered as authentic long duration, single use only, time-capsules.

All currently available prior art have similar removable stopper/lid/cover arrangements in that they are specifically designed to be opened intact to remove the contents and therefore capable of being reused for a similar purpose. Which is a critically important security problem associated with them. Other problems associated with these other containers include their susceptibility to, corrosion, seal leakage, breakage of external lips, rims, spouts, edges, and other protrudences, ease of access enabling casual tampering, theft due to the high recycle value of the expensive material they are made from and degradation over time when exposed to harsh environments, as such they do not offer sufficient extremely long term protection of the internal contents of the container.

Recent decades have shown tremendous advances in the field of medical sciences, which has subsequently resulted in the development of increasingly advanced cloning techniques. Since then there is a common perception among the community that future technologies will develop the ability to clone a full human being or other animals from a biological sample comprising viable DNA. This perception itself has already resulted in the storing of various biological specimens and DNA material from human and other various life forms in commercial industrial type facilities commonly called 'cryogenic facilities' which preserve the samples using expensive to operate freezing methods. The problem with this method of storage is on-going service costs charged by these cryogenic storage facilities because they consume huge amounts of energy and are extremely expensive to operate and are therefore economically restricted to governments and/or extremely wealthy individuals. They are clearly not intended to be for private use, and have relatively short facility operational life as they are only viable while electrical power and human attendants are available to run and to maintain the refrigeration equipment containing the samples, which in relation to time may only be a century at best or until the money paid to store the samples ceases.

Prior art containers and time capsules, funeral urns and similar containers are commonly significantly expensive, as they are made of materials such as aluminium, stainless steel, lead or other valuable metals. Moreover, such prior art receptacles are clearly designed to be reopened and reused or recycled after a predetermined period of time has lapsed. Therefore, there is a need for an alternative container for private individuals to store at least one biological sample or a sample donated from a person and/or persons, if possible still living, wishing to store the same for an indefinite or prolonged period of time. Where the container is fabricated from a relatively low cost, low recycle value material and is permanently sealed in a manner in which the container cannot be reused by anyone else in the future. In fact the only way in which to open the container, once sealed by the original owner, will be to break open the container itself, thus destroying any chance of reuse. It is envisaged the only reason to break open the container in the future will be that the opener intentionally intends to use the DNA contents for cloning or for legal proof of linage. Specifically, it is recognized that for such a container to achieve the purpose of acting as a time capsule for a person wishing to store a sample of their and/or their loved ones DNA in the hope of future regeneration it must have qualities that detract and avoid potential future destruction of both the container and DNA samples caused by the container being recycled for the material it's made from and/or reused by another person in the future. The container must therefore be of relatively no value to anyone else, (even as scrap value), contain no monetary valuables, nor information detailing the DNA donors prior identity and must clearly not be able to be opened without totally destroying the sealing capability of the container therefore rendering the container irreparable and useless to anyone in the future who simply wants to sell it on or reuse it for their own similar time capsule purposes.

OBJECT OF THE INVENTION

It is the object of the invention to ameliorate some or all of the above disadvantages of the prior art containers by providing a novel and innovative permanently sealed non-reusable container or vessel for containing a substance of interest, such as but not limited to, at least one biological sample containing DNA, and thus provide the general public with a method whereby a person or persons can have private and confidential management of their own, their family's and/or loved one's unique DNA samples.

STATEMENT OF INVENTION

In one aspect, the present invention resides in a permanently and hermetically sealed non-reusable container for at least one biological sample containing DNA material, comprising::
  a substantially thick walled vessel;
  the vessel having a void or chamber with a tapered entry, said chamber configured to house glass vials each containing at least one biological sample;
  the void or chamber containing a shock absorption material to protect the vials from breakage;
  a plug having a complementary external tapered configuration corresponding to that of the tapered entry,
  said tapered plug and entry having opposed peripheral grooves that are aligned to form a keyway when the plug is in position in the entry to cap the void or chamber,
wherein a hard-setting sealing compound used to seal the plug in the vessel forms a keyed ring in the keyway formed by the opposing grooves thereby permanently and hermetically sealing the plug in the vessel.

Preferably, the container is made of ceramic, pottery clay, moulded high density plastic resin or equivalent dense material. In the alternative cement, high grade plaster, fibreglass, high density injection moulded plastic, glass or non-ferrous metals or combinations thereof.

Preferably, the vessel or container is of a spherical configuration.

Preferably, the plug is made of the same material as the container.

Preferably, the plug has an internal chamber containing a loose element typically a ball bearing to provide a rattle or noise when the sealed or plugged vessel or container is shaken.

Preferably, the sealing compound is a hard setting material, such as dental plaster cement or plastic resin paste, which provides when set hard, an air tight and hermetical seal to secure the plug permanently inside the container.

Preferably, the glass vials are individually air tight.

Preferably, the shock absorbent material can be any known material which attenuates vibration and will not break-down and disintegrate over time.

Preferably, the plug comprises an outer peripheral surface, wherein when the plug is matted with the receptacle of the container, the outer peripheral surface aligns with the outer surface of the container such that the completed container has a substantially smooth outer surface.

Preferably, the container or plug has an internal void containing a loose element adapted to provide a rattle or noise when the container sealed with the plug is shaken.

BRIEF DESCRIPTION OF THE DRAWINGS

In order for the invention to be better understood and put to practical effect, reference will now be made to the accompanying drawings, wherein:
FIG. 1 shows a cross section of a preferred embodiment of the invention.
FIG. 2 shows a plan view of the plug of the invention of FIG. 1, and
FIG. 3 shows a sectional view through sectional line AA of FIG. 1.

DETAILED DESCRIPTION

Referring now to FIG. 1 there is shown a cross sectional view through a preferred example of a permanently sealed non reusable container according to the present invention. While it is shown that the container or vessel 1 is spherical in configuration, those skilled in the art would appreciate that the overall shape, size and overall dimensions of the container are not overly limited. Specifically, the person skilled would be able to routinely fabricate the vessel or container 1 into any final external configuration as desired, where the size would ultimately depend on the amount of the item of interest the container is to house when in use. As can be seen best in FIG. 1, the container or vessel 1 has a substantially thick outer wall, where the container or vessel is of a solid construction having an internal void or chamber 4 defined therein. As will be appreciated, the thickness of the outer wall of the container or vessel would not be overly limited, but should provide sufficient structural integrity to the container or vessel. It is envisaged that there could be a plurality of voids or chambers 4 formed in the container or vessel without departing from the spirit of the present invention. However, by way of example throughout the remainder of the Detailed Description reference will be made to an embodiment having only a single chamber or void 4.

While those skilled in the art will appreciate that the material the container is made of is not overly limited, it is envisaged in preferred embodiments that the container would be suitably fabricated from ceramic, pottery clay, moulded high density plastic resin or equivalent dense material. Alternatively, high grade plasters, fibreglass, high density injection moulded plastic, glass or non-ferrous metals or combinations thereof could also be used without departing from the spirit of the present invention. It is contemplated, however, that in preferred embodiments, the selected material would permit the sealed container to sink when placed in the liquid, which would assist a person in placing the item for future discovery.

Once again referring to FIG. 1, a stopper or plug 2 is provided to be used in conjunction with the vessel 1. The stopper or plug 2 is shown to be of a tapered configuration with a peripheral groove 7, where such is configured to be inserted into a tapered entry 3 formed in the vessel 1. Peripheral groove 7 of the plug 2 and circumferential groove (10, 8) of the vessel 1, will in use be aligned to form a keyway when the plug is completely inserted into the tapered entry 3 of the vessel 1. Dental cement could be used to fill the grooves 7, 8 to permanently secure the plug in the entrance, wherein the dental cement in the grooves 7, 8 forms a rock-hard captive peripheral ring or key which is permanently located in the keyway to prevent the stopper from being removed once the cement has set. While it is envisaged that dental cement could be used, it is to be understood that any known long-life and hard setting adhesive, cement or resin (e.g. epoxy resin) could be used as a sealing compound for the aforementioned purpose of preventing the stopper from being removed once the cement or adhesive has completely set. However, it should be understood that preferably the sealing compound would cure in a hard consistency and would not be susceptible to degradation over time, so as to significantly extend the lifetime of the time capsule of the present invention.

It should be appreciated that when the stopper or plug 2 is matted with the receptacle of the container or vessel 1, the outer peripheral surface of each respective element will align such that the completed time-capsule will have a substantially smooth outer surface. In this manner and when the sealing compound is set to complete the bond between the vessel and the stopper or plug, there would be no means by which to leverage the stopper out of its matting attachment with the vessel. In fact, once completely sealed the time capsule would not be able to be opened without actually breaking the container itself, and thus would not be reusable.

As is shown in FIG. 1, the stopper is also shown with an inert object, preferably a ball bearing 9a, which is permanently encapsulated in an internal chamber 9 of the plug 2 so as to provide a rattle when and if the vessel with the plug is shaken. It is envisaged that this internal rattle noise will indicate to a distant future finder the object is man-made and has an item of interest inside should the outer surface be significant degraded or the container's surface is obscured and covered in marine growth, after a prolonged period of time underwater, or coated with other natural debris associated with being buried underground.

As is shown best in FIG. 1, the vessel 1 has an internal void or chamber 4 formed therein, which is sized and configured to house an item of interest. It should be understood that the item of interest could be any item that the user desires to securely store in the vessel or container for a prologued period of time. While the item of interest is not overly limited, throughout the remainder of the specification and as shown in the Figures reference will be made to the item of interest being glass vials 5 containing biological samples containing DNA material, which is a preferred embodiment of the present invention.

The biological samples containing DNA material, in this example, are housed in glass vials 5, it is envisaged that the vials would be surrounded by a shock absorbent material 6 also housed within the internal void, filled up to the base of the stopper/plug. Examples of a shock absorbent material include but are not limited to materials such as dry sand, dry plaster or natural resins where such would be inert, significantly inexpensive and is by its nature immune to degradation over time. It is contemplated that the absorbent material could also suitably be soil or earth taken from a location having deep meaning for the sample donor, such as; from the country of origin, the town where the person/s were born, or another place having sentimental value.

Moving now to FIG. 2, which shows a plan view of a preferred container or vessel shown in FIG. 1, the peripheral groove 7 in the plug 2 is shown by broken line. The relative central position of the rattle mechanism of the plug is shown by 9, which as indicated previously houses the ball bearing 9a. FIG. 3 shows a cross sectional view through section line AA of the vessel of FIG. 1. The plan view of FIG. 3 shows the vials 5, in this case there are only four vials depicted completely encased in shock absorbent material 6. inside the inner chamber of the vessel. It will be obvious on inserting the plug to seal the vessel with dental cement or other adhesive that the vials will be completely encapsulated in the middle of the vessel in a contamination free inert and air tight environment. The tapered configuration of the plug 2 shown in FIG. 1 and FIG. 2 is designed so that air is evacuated from the void between the inner chamber (filled with the glass vials and absorbent material) and the plug inner base as the plug is inserted into the complementary tapered entry of the vessel.

It will be appreciated that the time-capsule, vessel or container described is intended to store and preserve, in an air-tight contamination free environment, the biological samples of a single person, several or many individuals and/or animal/s, either for the purpose of memorial or in the belief that future technologies and societies will permit and encourage cloning regeneration. As such, it provides a convenient, simple to use, environment friendly, cost effective method by which an individual, or family or group of friends can manage and deposit, in the privacy of their own home, their own or loved one's DNA in a container which is designed to last, if left undisturbed, not just their lifetimes but for thousands of years.

For instance if used as a memorial the guaranteed authenticity of the contents would hold significantly more emotional attachment than an urn containing lifeless ashes. If used as a time capsule for those people that believe future medical research will develop sufficiently to successfully clone a person's body, the present invention can offer a private, convenient, and a more economically available alternative to costly cryogenic freezing preservation. The time-capsule of the present invention can offer to lovers, of all persuasions, a personal romantic love symbol confirming their love/relationship is everlasting by sealing their DNA samples within the capsule, which if left undisturbed will last thousands of years. Whole families can achieve a similar purpose. In essence, a small part of every family member, (via a DNA sample taken from each member while the donors are still young) can be stored together 'forever' within a single family DNA time capsule. A personal DNA time-capsule can also become a psychological comfort to the elderly and devoted pet owners who never want to be parted when one or the other passes away first. A personal DNA time-capsule can be confidently placed within a burial coffin as it is unaffected by natural body decomposition, or similarly be deposited with other family member's personal DNA time-capsules within family crypts, both as a final resting place, and if required for legal reasons in the future, to prove DNA linage. Much larger versions could accommodate many hundreds of glass vials with the DNA samples of large groups, such as complete sporting teams and their families, or whole communities. It is envisaged that the outside of the container could be decorated by any known means available to those skilled in art so as to increase the aesthetics of the container.

It will of course be realised that while the foregoing has been given by way of illustrative example of this invention, all such and other modifications and variations thereto as would be apparent to persons skilled in the art are deemed to fall within the broad scope and ambit of this invention as is herein set forth.

In the specification the terms "comprising" and "containing" shall be understood to have a broad meaning similar to the term "including" and will be understood to imply the inclusion of a stated integer or step or group of integers or steps but not the exclusion of any other integer or step or group of integers or steps. This definition also applies to variations on the terms "comprising" and "containing" such as "comprise", "comprises", "contain" and "contains".

The invention claimed is:

1. A permanently and hermetically sealed container for at least one biological sample containing DNA comprising:
   (a) a substantially thick walled vessel, having a void or chamber with a tapered entry, said chamber configured to house glass vials each containing at least one biological sample, wherein the void or chamber contains a shock absorption material to protect the vials from breakage; and
   (b) a plug having a complementary external tapered configuration corresponding to that of the tapered entry, said tapered plug and entry having opposed peripheral grooves that are aligned to form a keyway when the plug is in position in the entry to cap the void or chamber,
   wherein a hard-setting sealing compound used to seal the plug in the vessel forms a keyed ring in the keyway formed by the opposing grooves thereby permanently and hermetically sealing the plug in the vessel;
   wherein the plug comprises an outer peripheral surface, wherein when the plug is matted with the receptacle of the container, the outer peripheral surface aligns with an outer surface of the container such that the completed container has a substantially smooth outer surface; and
   wherein the container or plug has an internal void containing a loose element adapted to provide a rattle or noise when the container sealed with the plug is shaken.

2. The container according to claim 1 wherein the vessel is fabricated from ceramic clay, pottery clay, moulded plastic resin, high-density injection moulded plastic or a combination thereof.

3. The container according to claim 1 wherein the vessel or container is of a spherical configuration.

4. The container according to claim 1 wherein the plug is made of the same material as the container.

5. The container according to claim 1 wherein the loose element is at least one ball bearing.

6. The container according to claim 1 wherein the hard-setting sealing compound or adhesive provides a permanent, inert air tight and hermetical seal for the plug in the container.

7. The container according to claim 1 wherein the vials are glass vials individually sealed using an inert stopper.

8. The container or vessel according to claim 1 wherein the shock absorbent material is selected from the ground consisting of dry plaster, dry sand, natural resin, 'homeland' soil, and/or combinations thereof.

* * * * *